United States Patent [19]

Taniura et al.

[11] Patent Number: 5,278,343

[45] Date of Patent: Jan. 11, 1994

[54] PROCESS FOR PRODUCING 2-METHYL-1-NAPHTHOL

[75] Inventors: Masato Taniura, Kitakanabara; Yoshin Tamai, Shibata, both of Japan

[73] Assignee: Kuraray Company, Ltd., Kurashiki, Japan

[21] Appl. No.: 20,750

[22] Filed: Feb. 22, 1993

[30] Foreign Application Priority Data

Feb. 27, 1992 [JP] Japan .................................. 4-076064

[51] Int. Cl.[5] .............................................. C07C 37/07
[52] U.S. Cl. .................................... 568/736; 568/313
[58] Field of Search ........................ 568/736, 313, 783

[56] References Cited

U.S. PATENT DOCUMENTS 3,993,701  11/1976  Leach et al. ........................ 568/736

FOREIGN PATENT DOCUMENTS 0201071  11/1986  European Pat. Off. .
2421745  11/1975  Fed. Rep. of Germany .
2612076   3/1977  Fed. Rep. of Germany .

*Primary Examiner*—James H. Reamer
*Attorney, Agent, or Firm*—Oblon, Spivak, McClelland, Maier & Neustadt

[57] ABSTRACT

2-Methyl-1-naphthol is obtained by isomerization of 2-methylene-1-tetralone. For the isomerization of 2-methylene-1-tetralone there is used a Pd-, Rh- or Ru-based catalyst that has been previously treated with hydrogen gas. 2-Methylene-1-tetralone synthesized from 1-tetralone by the Mannich reaction can be used for this purpose.

16 Claims, No Drawings

PROCESS FOR PRODUCING 2-METHYL-1-NAPHTHOL

BACKGROUND OF THE INVENTION

1. Field of the Invention

The present invention relates to a process for producing 2-methyl-1-naphthol, which is useful as an intermediate for producing medical pharmaceuticals, such as menadione (Vitamin $K_3$) and Vitamins $K_1$ and $K_2$.

2. Description of the Related Art

Known processes for synthesizing 2-methyl-1-naphthol are those utilizing as starting materials ① 1-naphthol, ② 2-methylnaphthalene and ③ 1-tetralone.

The process with the above ① comprises permitting methanol to add to 1-naphthol in gaseous phase in the presence of (i) $Al_2O_3$ (U.S. Pat. No. 3,993,701, Switz. Pat. No. 598170), (ii) $Fe_2O_3$ or $Cr_2O_3$ (Chem. Pharm. Bull., 24(9), 2199 (1 976) (iii) a combination of cerium oxide and an oxide of a metal such as antimony, germanium, tin or magnesium (Japanese Patent Application Laid-open No. 47958/1975) or like catalysts. This process has the drawbacks of requiring, generally, a high temperature of 325° to 425° C. and generation of a large amount of by-products. There has also been reported an attempt to methylate the naphthol with a methylation agent such as an organic lithium and methyl iodide or dimethyl sulfate (Indian J. Chem., Sect. B, 21B (5), 474 (1982); J. Org. Chem., 53 (22), 5345 (1988)). This is an uneconimical process because of low yield.

The process with ② 2-methylnaphthalene comprises converting it with formic acid, acetic acid or propionic acid to the corresponding naphthyl ester by electrochemical reaction and then hydrolizing it into 2-methyl-1-naphthol (DE 2434845). This process also suffers a low yield and cannot be said to be suitable for commercial production.

An example of the process with ③ 1-tetralone comprises converting 1-tetralone to 2-methyl-1-tetralone and then dehydrogenating it by heating in the presence of Pd/C (Japanese Patent Application Laid-open No. 65235/1983), while another one comprises the successive steps of converting 1-tetralone to 2-benzoyloxymethylene-1-tetralone, subjecting it to hydrogenolysis in the presence of Pd/C and cyclohexene and isomerizing the resulting product (Chem. Ind., 14 , 5052 (1981)). However, there is a limit to the yield of monomethylation of 1-tetralone with the former process, and the latter is uneconomical because of long reaction paths.

SUMMARY OF THE INVENTION

Accordingly, an object of the present invention is to solve the above problems of the prior art and to provide a process for producing, economically, 2-methyl-1-naphthol from a raw material which is readily available and inexpensive.

Thus, the present invention provides a process for producing 2-methyl-1-naphthol which comprises converting 2-methylene-1-tetralone to 2-methyl-1-naphthol by isomerization.

DETAILED DESCRIPTION OF THE PREFERRED EMBODIMENTS

2-Methylene-1-tetralone used in the present invention can be synthesized from 1-tetralone by the Mannich reaction. This is generally effected by reacting formaldehyde with 1-tetralone in the presence of a secondary amine and a carboxylic acid. The reaction temperature is preferably 50° to 150° C., more preferably 60° to 110° C.

Examples of the secondary amine used in the reaction are dimethylamine, diethylamine, dipropylamine, di-n-butylamine, pyrrolidine, piperidine, morpholine and N-methylaniline, among which dipropylamine and di-n-butylamine are preferred because of high reactivity produced with them.

Any carboxylic acid can be used for the above reaction, but it is desirable to use acetic acid, propionic acid or butyric acid in view of ready recovery.

Formaldehyde is available in the form of formalin, paraformaldehyde or trioxane, any one of which may be used in the reaction. Formalin is, however, most desirable in view of reactivity and commercial availability.

The solvent used in the reaction may either be polar or non-polar. Examples of desirable polar solvents are cyclic ethers such as tetrahydrofuran and dioxane and those of desirable non-polar solvents are aromatic hydrocarbons such as benzene, toluene and xylene. Where a solvent is used, it is recommendable to adjust the amount such that the concentration of the reaction product 2-methylene-1-tetralone will become 1 to 30%, preferably 5 to 20%.

The secondary amine and carboxylic acid can each be used in an amount of 0.05 to 3 molar equivalents based on the moles of 1-tetralone, and preferably 1 to 2 molar equivalents on the same basis from the viewpoints of reaction rate and economy.

It is desirable to use formaldehyde in an amount of 0.1 to 2.0 molar equivalents based on the moles of 1-tetralone, in particular in an amount of 0.5 to 1 molar equivalent on the same basis, to minimize the amount of formaldehyde remaining after the reaction.

After completion of the Mannich reaction of 1-tetralone, the secondary amine and carboxylic acid can be recovered in the following manner. Let us choose a case where, for example, acetic acid has been used as a carboxylic acid. Water is added to the reaction mixture, which causes the acetic acid and most of the secondary amine to be distributed to the water layer. The water layer is then distilled, to recover these compounds, and the rest of the secondary amine is recovered by washing the organic layer containing it with an aqueous acetic acid.

Simple washing with water, an organic acid or an inorganic acid of the reaction mixture resulting from the reaction can remove the amine which would become a catalyst poison upon the succeeding isomerization of 2-methylene-1-tetralone. The reaction mixture after this washing can be, as it is, subjected to the isomerization of 2-methylene-1-tetralone.

The isomerization of 2-methylene-1-tetralone is desirably effected in the presence of a Pd-, Rh- or Ru-based catalyst that has been treated with hydrogen gas beforehand, which realizes, even under mild reaction conditions, rapid reaction and a high yield.

The Pd-based catalyst usable for this purpose desirably is in a form on a carrier, and its examples are Pd/C, $Pd/Al_2O_3$, $Pd/BaCO_3$ and $Pd/CaCO_3$. Recommendable Rh-based catalysts are those in the form of complexes, and their examples are $RhCl(PPh_3)_3$, $RhH(CO)(PPh_3)_3$, $RhH(PPh_3)_4$ and $Rh_2Cl_2(C_2H_4)_4$. Recommendable Ru-based catalyst are also complexes, examples of which are $RuCl_2(PPh_3)_3$, $RuClH(CO)(PPh_3)_3$ and $RuH_2(PPh_3)_4$.

These catalysts are generally used in an amount of ratio by weight of 0.1 to 20 based on the weight of 2-methylene-1-tetralone.

The pretreatment of these catalysts with hydrogen gas may be performed in the reaction solvent used, under atmospheric pressure or under pressure and at a temperature of 0° to 150° C., and even simply passing hydrogen at room temperature and under atmospheric pressure can produce an isomerization catalyst that can meet the purpose of the present invention. The isomerization catalyst having been used in the reaction can become usable again by treatment with hydrogen gas.

The solvent for isomerization may either polar or non-polar and, gene(rally, the same solvent as used in the Mannich reaction of 1-tetralone can be used. That is, cyclic ethers such as tetrahydrofuran and dioxane can be used as polar solvents and aromatic hydrocarbons such as benzene, toluene and xylene as non-polar solvents.

The isomerization can be effected by suspending the hydrogen gas-pretreated catalyst in a reaction solvent, adding the reaction substrate to the suspension and then heating the mixture up to a prescribed temperature. The reaction temperature is preferably 50° to 150° C., more preferably 80° to 110° C.

The reaction is preferably effected under an atmosphere of an inert gas such as nitrogen or argon. With the isomerization effected under an atmosphere of hydrogen, rapid conversion of the reaction substrate occurs even at a room temperature to form 2-methyl-1-tetralone with the methylene group having been hydrogenated.

If the isomerization is conducted with a catalyst that has not been treated with hydrogen gas, the isomerization will proceed very slow or will not proceed at all to form a dimer, whereby the yield decreases.

The isomerization may be effected either by batch system or continuous system.

After completion of the isomerization, 2-methyl-1-naphthol can be isolated and recovered by distillation.

Other features of the invention will become apparent in the course of the following descriptions of exemplary embodiments which are given for illustration of the invention and are not intended to be limiting thereof.

EXAMPLES

Example 1

1) Synthesis of 2-methylene-1-tetralone

A 100-ml pressure-proof glass reaction vessel was charged with 2.92 g (0.02 mole) of 1-tetralone, 2.59 g (0.02 mole) of di-n-butylamine, 1.20 g (0.02 mole) of acetic acid and 15 ml of toluene. To the mixture 0.974 g (0.012 mole) of an 37% aqueous formaldehyde solution was added and the vessel was sealed and heated up to 90° C. After maintaining the temperature at 90° C. for 30 minutes, the vessel was cooled to room temperature. The contents were separated by addition of 5 ml of water, and the water layer was washed off with a 50% aqueous acetic acid solution. The toluene layer was further washed with a 10% aqueous hydrochloric acid, saturated aqueous $NaHCO_3$ solution and saturated aqueous sodium chloride solution, to give a solution of 2-methylene-1-tetralone in toluene. The reaction mixture was analyzed by GLC and its composition was found to be 1.45 g of 2-methylene-1-tetralone and 1.16 g of unreacted 1-tetralone (the conversion of 1-tetralone: 60.2%; selectivity: 82.1%).

2) Isomerization of 2-methylene-1-tetralone

A 50-ml reaction vessel was charged with 20 ml of toluene and 100 mg of 5% Pd/C (dry type) and hydrogen gas was passed through the mixture at room temperature. After conducting activation for 1 hour, the atmosphere in the vessel was replaced with nitrogen and the vessel was heated to 110° C. To the mixture a solution of 1.25 g (7.9 mmoles) of 2-methylene-1-tetralone in 20 ml of toluene was added dropwise over 2 hours. After the addition, refluxing state was maintained for further 1 hour to permit the reaction to proceed until completion. GLC analysis revealed that there was formed 1.23 g of 2-methyl-1-naphthol (conversion: 98.5%; selectivity: 100%).

Example 2

A 50-ml reaction vessel was charged with 10 ml of toluene and 10 mg of $RhCl(PPh_3)$, and hydrogen gas was passed through the mixture at room temperature. After conducting activation for 1 hour, the atmosphere in the vessel was replaced with nitrogen and the vessel was heated to 90° C. To the mixture 300 mg (1.9 remoles) of 2-methylene-1-tetralone was added and reaction was effected at 90° C. for 3 hours. GLC analysis revealed that the conversion was 14.7% and the selectivity 62.3%.

Example 3

A 50-ml reaction vessel was charged with 10 ml of toluene and 10 mg of $RuCl_2(PPh_3)_3$, and hydrogen gas was passed through the mixture at room temperature. After conducting activation for 2 hours, the atmosphere in the vessel was replaced with nitrogen and the vessel was heated to 90° C. To the mixture 300 mg (1.9 remoles) of 2-methylene-1-tetralone was added and reaction was effected at 90° C. for 4 hours. GLC analysis revealed that the conversion was 80.9% and the selectivity 72.3%.

Example 4

A 50-ml reaction vessel was charged with 10 ml of toluene, 1 00 mg of 5% Pd/C (dry type) and 0. 26 g (1.7 remoles) of 2-methylene-1-tetralone and the air in the vessel was replaced by nitrogen. The vessel was heated up to a temperature of 110° C. and reaction was effected for 8.5 hours. GLC analysis revealed that the conversion was 32.5% and the selectivity to 2-methyl-1-naphthol was 73.3%.

Example 5

A 50-ml reaction vessel was charged with 8 ml of toluene, 5 mg of 5% Pd/C (dry type) and 0.21 g (1.3 mmoles) of 2-methylene-1-tetralone, and hydrogen gas was passed through the mixture at room temperature with stirring. After 3 hours and 45 minutes, when the spot of the starting material disappeared, the reaction was terminated. GLC analysis revealed that the conversion was 100% and the selectivity to 2-methyl-1-naphthol was 29.5% (that to 2-methyl-1-tetralone: 80.5%).

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing 2-methyl-1-naphthol, which comprises isomerizing 2-methylene-1-tetralone to 2-methyl-1-naphthol at a temperature effective therefor in the presence of a Pd-, Rh- or Ru-based catalyst that has been previously treated with an amount of hydrogen gas effective to promote said isomerization.

2. The process according to claim 1, wherein said Pd-, Rh- or Ru-based catalyst that has been previously treated with hydrogen gas is used in an amount of ratio by weight of 0.1 to 20 based on the weight of 2-methylene-1-tetralone.

3. The process according to claim 1, wherein said isomerization is conducted at a temperature of about 50° to 150° C.

4. The process according to claim 3, wherein said isomerization is conducted at a temperature of about 80° to 110° C.

5. The process according to claim 1, wherein said 2-methylene-1-tetralone has been synthesized from 1-tetralone by reacting formaldehyde with 1-tetralone in the presence of a secondary amine and a carboxylic acid.

6. The process according to claim 5, wherein said secondary amine is selected from the group consisting of dimethylamine, diethylamine, dipropylamine, di-n-butylamine, pyrrolidine, piperidine, morpholine and N-methylaniline.

7. The process according to claim 6, wherein said secondary amine is dipropylamine or di-n-butylamine.

8. The process according to claim 5, wherein said formaldehyde is used in the form of formalin, paraformaldehyde or trioxane.

9. The process according to claim 8, wherein said formaldehyde is used in the form of formalin.

10. The process according to claim 1, wherein said Pd-based catalyst is selected from the group consisting of Pd/C, Pd/Al$_2$O$_3$, PD/BaCO$_3$ and Pd/CaCO$_3$.

11. The process according to claim 1, wherein said Rh-based catalyst is selected from the group consisting of RhCl(PPh$_3$)$_3$, RhH(CO)(PPh$_3$)$_3$, RhH(PPh$_3$)$_4$ and Rh$_2$Cl$_2$(C$_2$H$_4$)$_4$.

12. The process according to claim 1, wherein said Ru-based catalyst is selected from the group consisting of RuCl$_2$(PPh$_3$)$_3$, RuClH(CO)(PPh$_3$)$_3$ and RuH$_2$(PPh$_3$)$_4$.

13. The process according to claim 1, wherein said previous treatment of said catalyst with hydrogen comprises contacting said catalyst with said hydrogen gas.

14. The process according to claim 1, which is conducted in an organic solvent.

15. The process according to claim 14, wherein said organic solvent is selected from the group consisting of tetrahydrofuran, dioxane, benzene, toluene and xylene.

16. The process according to claim 1, which is conducted under an inert gas.

* * * * *